United States Patent [19]

Chackal

[11] Patent Number: 5,135,771
[45] Date of Patent: Aug. 4, 1992

[54] METHOD AND COMPOSITION FOR PROLONGING SHELF-LIFE OF CUT FLOWERS

[75] Inventor: Julian F. Chackal, Pincourt, Canada

[73] Assignee: Vie-Rose, Inc., Saratoga Springs, N.Y.

[21] Appl. No.: 641,178

[22] Filed: Jan. 15, 1991

[51] Int. Cl.$^5$ ............................................. A01G 5/06
[52] U.S. Cl. ........................................ 427/4; 426/106; 47/62; 47/84; 47/41.13; 71/68; 73/73
[58] Field of Search ................. 427/4; 426/106; 47/41.13, 62, 84, DIG. 3, DIG. 11; 73/432.1, 73; 71/68

[56] References Cited

U.S. PATENT DOCUMENTS

| | | | |
|---|---|---|---|
| 1,076,786 | 10/1913 | Reinherz | 427/21 |
| 1,909,013 | 5/1933 | Ruzicka | 426/106 |
| 2,971,292 | 2/1961 | Malecki | 71/68 |
| 2,994,424 | 8/1961 | Selby et al. | 426/106 |
| 3,173,880 | 3/1965 | Pappas et al. | 73/73 |
| 3,314,194 | 4/1967 | Halleck | 47/84 |
| 3,320,046 | 5/1967 | Siegel | 71/68 |
| 3,518,096 | 6/1970 | Layton | 71/68 |
| 3,678,621 | 7/1972 | Reams | 71/68 |
| 3,842,539 | 10/1974 | Sacalis | 71/68 |
| 3,895,140 | 7/1975 | Sheldon et al. | 428/22 |
| 3,929,448 | 12/1975 | Brantley | 71/68 |
| 3,952,584 | 4/1976 | Lichstein | 73/73 |
| 4,256,773 | 3/1981 | Itoga et al. | 71/68 |
| 4,382,380 | 5/1983 | Martin | 73/73 |
| 4,710,394 | 12/1987 | Sellegaard | 427/4 |
| 4,827,663 | 5/1989 | Stern | 47/41.13 |

Primary Examiner—Shrive Beck
Assistant Examiner—Diana L. Dudash
Attorney, Agent, or Firm—Schmeiser, Morelle & Watts

[57] ABSTRACT

Method and composition for retarding bloom development thereby extending shelf life of fresh cut flowers (16) by "blanketing" and "feeding" techniques. Fresh cut flowers, typified by roses are refrigerated and provided a blanketing confinement within a close environment of an essence of aromatic flower (such as lavender or rose) by the presence of essential flower oils or real aromatic flowers. The essence is, effectively, a vapor blanket. Cut stemmed (10) flowers are initially transported, stored or displayed in a container (18') of fresh water (19), in which a light or expanded magnesium carbonate sediment layer (21) provides cut flower end (14') envelopment for bacterial filtration, oxygen buffering and sufficient water-borne nutritional intake with or without the adjunct blanketing. Additionally, freshness is made determinable by a simple testing process which will anticipate the value of applying or reapplying the carbonate treatment technique.

10 Claims, 1 Drawing Sheet

METHOD AND COMPOSITION FOR PROLONGING SHELF-LIFE OF CUT FLOWERS

BACKGROUND OF THE INVENTION

1. Field Of The Invention

This invention relates generally to a method for preserving fresh cut flowers and, specifically, to extending shelf lives, as defined herein, by providing methodology that treats cut flowers, depending upon freshness (and with a test for determining same), so as to acquire more predictable and extended shelf lives heretofore unattainable by floriculturists and/or professional florists.

2. Background Art

Methods abound for the prolongation, that is, extension of shelf life duration for cut flowers and other plants which have been separated from their natural form of sustenance. Commonly, sugar solutions, to which have been added some form of mineral or organic acid ingredients, have been used for immersing therein freshly cut floral stems. With particular regard to cut roses, the bloom which enjoys the highest demand and provides the greatest profit, a fresh rose displayed in such commercially available nutrients may last up to ten days. If the flower is not absolutely fresh (may be normally up to 5-7 days old), the best available nutrient for display cannot sustain the flower beyond three days; and, under best environmental conditions, will still be unable to attain the fullest bloom.

I have been in the business of providing florists with cut flowers of several varieties for more than 15 years. During this time, it has been apparent that the state of freshness and quality of blooming displayed by many florists, especially outside large cities where it is more difficult for florists to receive absolutely fresh flowers (notably, roses), is generally far less than that desired. Of utmost concern is the need to promote flower bloom, in much the fashion as when it is on the shrub, enduring longer than normal in cold storage and on the display shelf. Thus, the main thrust of the instant invention is to retard oxidation while providing nourishment, at the base of the stem of a fresh cut flower, while concurrently limiting direct contact of the cut portion with water. The reason for this will be disclosed hereinafter; but, suffice it to say, that the provision of nourishment, according to the instant invention, and with or without adjunct preservational aids will allow roses and other kinds of flowers to bloom fully, but more slowly. After cutting, they live longer under a mild refrigeration of about 40° F. Aside from using a mineral compound in levigated state, this disclosure will depart radically from the prior disclosures of floral preservation techniques.

Relative to earlier disclosures, an intensive search of the patent and professional floral/horticultural literature has failed to disclose any of the methods or specific constituents used in the instant invention. In a patent issued to Sellegaard in December 1987, U.S. Pat. No. 4,710,394, there is disclosed a preparation and process for the preservation of plants. The method of Sellegaard, however, should not be confused with the instant invention as the former is analogous to embalming and not the extension of (bloomable) shelf life. Nevertheless, there is a similarity disclosed in that a combined carbonate of calcium and magnesium, with magnesium providing the lower weight contribution to the mixture, is used to prepare a solution in which the flower or plant to be preserved is immersed. Since the patentee expresses the need to dissolve the magnesium/calcium carbonate mixture in organic acid, citric acid is provided. Noteworthy in this disclosure is the fact that no aromatics, particularly esters or plant oils, are used for acquiring the specific results of the patentee. A much earlier patent, that issued to Reinherz in October 1913, U.S. Pat. No. 1,076,786, is drawn to a method for preserving plant leaves, flowers, butterflies and the like. As the title implies, the preservation is much akin to that of Sellegaard and, indeed, employs according to the patentee a carbonate of magnesium (in addition to oily matter, glycerine, and Venetian turpentine). As stated earlier, these patents disclose some of the constituents of the instant invention but fall far short of my goal of providing a method for sustaining a fresh cut flower, in the living bud state, as long as possible under mild refrigeration and prolonging its shelf life, allowing the bud to attain fullest bloom for a greatly extended period of time over the presently and conventionally realizable display life.

Before discussing the instant invention in detail, it is well for the reader to have an understanding and appreciation of the terminology that will be used hereinafter. The following terms shall have the indicated meanings unless such is modified in the text:

"Capillaries/capillary system" means the phloem (also, bast or liber) which is the complex plant tissue composed of sieve tubes. It is through this complex that the plant draws its nutrient; thus, the capillary system or phloem is of greater importance than the xylem, which is the woody portion of a plant stalk.

"Levigated" means an extremely finely ground mineral, in the range of 1.0-100.0 microns.

"Essence" means, specifically, oil of lavender or, generally, any oil or ester of an aromatic flower such as rose oil or lavender oil.

"Shelf life" means the total life of a flower from the time of its cutting (in the bud state) to the point of onset of any of the following conditions: stem or bud wilt; loss of full color; or loss of a major aesthetic characteristic such as petals or failure of the bud to achieve better than 50% of the normally expected (on the shrub) bloom. As discussed herein, "dormant shelf life" refers to that portion of the cut flower's life immediately after cutting at the incipient bud stage, during its refrigeration period and up to the point it is placed on display. Thereafter, shelf life includes, and is referred to as, the "display shelf life", which commences upon removal from refrigeration until the occurrence of one of the stages or events (as above) which signal the termination of the flower's shelf life.

SUMMARY OF THE INVENTION

By both serendipity and concerted experimentation, I have discovered a method that allows achievement of the aforementioned goals. Firstly, a test may be made on a cut rose or other showy flower which will allow one to immediately discern the flower's state of freshness. Empirically, the test evidences whether or not the cut flower is capable of undergoing nourishment intake by giving sign that the phloem or capillary system is functional. The freshly cut end of the stem is immersed for a certain period of time in an aqueous suspension of levigated silica. After immersion, the stem is removed and observed in the region of the cut. If in a nourishment intake state, an observer will see a circular layer of silica over the capillary system, that is on the phloem that is readily seen between the xylem and skin of the stem. If the circular layer of silica fails to appear after about 30 seconds, such will indicate that the rose or flower is not fresh and that a subsequently applied carbonate or feeding process of the instant invention will only be a salvaging procedure. Notwithstanding lack of freshness, the method of the invention will provide an efficacious salvage of the cut flower in that, as long as the flower appears fresh, the instant invention is capable of extending its remaining display shelf life up to at least twice the norm.

Immediately, or as soon as physically possible after the flowers are cut, the stem cuts are immersed in a levigated light magnesium carbonate, also known as expanded magnesium carbonate, which has been prepared in both the form and concentration necessary to assure that the fresh cut on the stem will be totally surrounded by the levigated, washed carbonate in accord with the hereinafter disclosed specific criteria. This is termed, for brevity, the "feeding" or "carbonate" technique.

Quite fortuitously during research, it was also discovered that the aromatic essence or perfume of an aromatic flower will retard, to great extent, the blooming of other cut flowers. Unfortunately, where there is a great deal of circulation, such an effect cannot be readily achieved; however, during refrigerated storage, or what is termed the dormant shelf life period, cut roses and similar flowers may be kept in a closed atmosphere in which they and one or more essences of vital aromatic oils (acquired from flowers also) may be confined. A cost expedient in the way of essential oils is oil of lavender; but, rose oil and oils of other aromatic flowers are also useful for this purpose.

It is during this stage that bloom retardation, especially of bud roses, is maximized and that these "carbonate" or "feeding" and "blanketing" techniques of the instant invention prove its value most noticeably. As will be hereinafter disclosed, the extension of dormant shelf life over the norm, by use of the invention, has clearly exceeded anything thusfar seen in the industry. The "blanketing" technique is optionally applied along with the "feeding" technique and is used immediately after the first cutting of the flower.

If freshness has been guaranteed by the aforementioned preservation techniques, the display shelf life will exceed two weeks; and, if the cut flower is already stale (as determined by the aforementioned testing process) it may still be salvaged to the extent that the normally remaining display shelf life can still be doubled, the fullest bloom may yet be attained and the stem will remain virtually vertical, with no signs of wilt, for the thereafter prolonged display shelf life.

DETAILED DESCRIPTION OF THE PREFERRED EMBODIMENT

General Procedures and Freshness Test

Figure 1A:
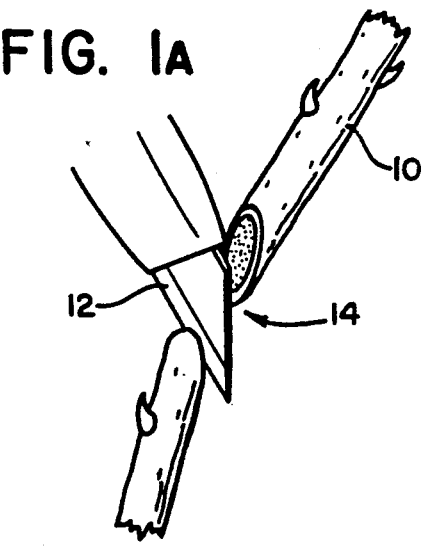
FIGS. 1A and 1B disclose a proper cut on a flower stem being prepared for the instant invention process.
Figure 1B:
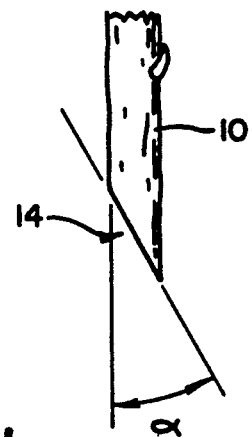

With reference being had to FIGS. 1A and 1B, there is illustrated, in the former, a typical florist's cutting of a flower stem 10, with a florists knife 12 being used to achieve the diagonal cut 14. In the latter, FIG. 1B, the stem 10 is seen cut 14 at an angle $\alpha$, wherein $\alpha$ lies somewhere between about 30° and about 60°. A regular transverse cut will generally suffice, however, to sever the bud flower from the plant or bush and such a cut reduces the amount of surface area that will both exude plant sap or, more importantly, allow the intrusion of bacteria. Upon application of the invention, however, the diagonal cut aforesaid may be used because harmful bacteria will be shut out by application of the carbonate technique.

The determination of freshness is not required normally; but, if the seller-florist is about to retail flowers not protected by the invention, or place them on display, this knowledge would be most helpful in maintaining customer satisfaction or minimizing advertising costs. As to the latter, an in-shop display, (which is essentially advertising) might better not have been made if the difference in display shelf lives (which might ensue because of the use of a stale flower) is more than a few days. Throughout the remainder of this disclosure, reference will be made to roses, bud roses or cut roses; but, it should be understood that this is not to the exclusion of other showy flowers.

Figure 2A:
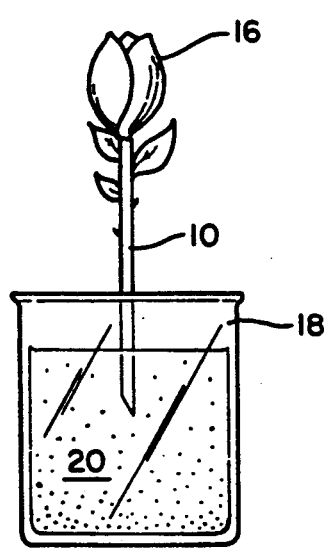
FIG. 2A is an illustration of the freshness test.
Figure 3A:
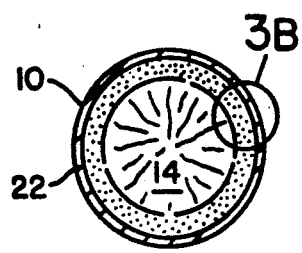
FIG. 3A and 3B are detailed illustrations of the stem end during a portion of the FIG. 2A test procedure.
Figure 3B:
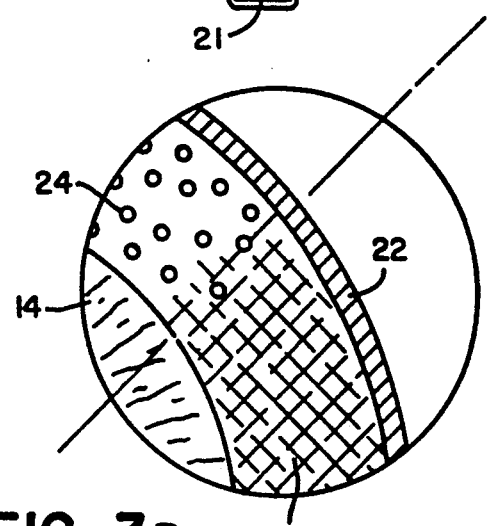

To detect the state of freshness in a cut flower, mix and retain in suspension about 50 grams of levigated silica (at 325 mesh) in about 300 cc of water. Keeping the silica in suspension, the stem of the rose (cut flower) is placed into the suspension and held there for 20 seconds. Then, immediately upon removal, the cut area is observed for the appearance of silica particles proximate the capillaries or phloem which has been exposed. FIGS. 2A and 3 are now referred to as illustrative of the procedure. The freshly cut flower stem 10 bearing the bud 16 is immersed in an aqueous suspension 20 within the glass/beaker 18 and held there for the requisite 20 seconds. It is removed thereafter and, reference being had to FIG. 3, observation is made of the freshly cut base area 14' of the stem 10 with particular attention being paid to the area proximate the skin 22-capillary 24 area. Within approximately 30 seconds, if the flower is in the nourishment mode, a pseudocrystalline "growth" 26 appears which is, in reality, the levigated silica being strained or sieved from the suspension; the water is taken up into the stem via the sieve tubes or phloem. The failure to obtain such results after 30 seconds indicates that the rose or flower is not fresh enough to benefit fully from the invention and that, as previously mentioned, the instant process for shelf life preservation and extension will only be a salvaging exercise. I hasten to point out, however, that even in a flower which is 5 to 7 days old, but still looks quite attractive in spite of its not having been treated with the invention at the first cutting, the hereinafter disclosed procedures for prolonging display shelf life will effect a notable reward over use of the currently best available nutrient, by providing an eight-day life versus three-day life, by still attaining the fullest bloom and by maintaining a non-wilting, vertical stem versus an untreated, stale flower's wilt within three days.

Carbonate (Feeding) Technique

A bud rose which has been treated with the dormant preservation method will enjoy up to two weeks or more of a highly aesthetic display shelf life, having a fuller display as the buds open slowly and more fully.

As pointed out earlier, even in the case where the rose or flower is not too fresh (attractive, but already 5-7 days old), the instant invention's display life-extension method will provide at least twice the display shelf life (over the normal, using best available nutrients) while resulting in the fullest bloom, with no appreciable stem wilt. In numerous attempts, using levigated minerals to form a sedimentary layer covered by water in which a rose or flower will stand, I have noted that obstruction of the vascular system (the phloem) prevents the water from reaching the flower regardless of the porosity of the sedimentary layer(s). In these cases, porosity is simply irrelevant because the first grains of the mineral(s) obstruct the capillary system or channels of suction (phloem). The grains of the particular minerals are not assimilated by the flower in its normal nourishment fashion. This applies to all minerals with which I experimented, except levigated magnesium carbonate, as used under specific conditions. It is essential that the carbonate of magnesium be employed which is described as magnesium carbonate, light, USP. I also refer to this as expanded magnesium carbonate because it is more than intrinsic $MgCO_3$. Best results are obtained in a levigated magnesium carbonate of the aforementioned type which is generally a combination of four molecules $MgCO_3$ to one molecule $Mg(OH)_2$ in a hydrated state. The analysis of this substance shows an MgO content of 41-42% and a loss of 56-56% on ignition. Also notably present is an acidic constituent, $SO_3$ at 0.1-0.3% and Cl at 0.08-0.1%. Levigation (grain size) is approximately 98.5 percent of 2.0 microns-20 microns, with smaller grain size (2.0 microns-6.3 microns) accounting for approximately 23%. The commercial grade of (expanded or) light magnesium carbonate used herein contains acidic constituents which must be removed. This carbonate, as obtained from commercial sources, is washed twice in a pure water using approximately 12 liters of water for every 250 grams of light magnesium carbonate. The carbonate is allowed to soak in the second wash for a few hours and washed then a third time with about 8 liters of preferably distilled water. The final washed product remains in the final rinse water with no attempt being made to dry, drain or use the carbonate in any other state such as dried powder or paste. Quite simply, once dry after the washing, the magnesium carbonate is useless; thus, it should remain in the final rinse water, retaining the hydrated state that results from the plurality of washings.

Figure 2B:
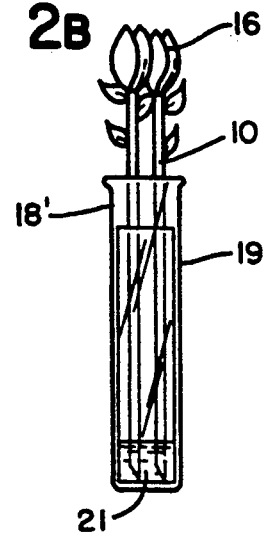
FIG. 2B is an illustration of the carbonate application technique of the invention.

Reference to FIG. 2B will demonstrate both the method and structural elements for applying the carbonate technique of the instant cut flower preservation method. A quantity of the sediment 21 and the final wash water 19 are placed in a tube/vial/vase 18' or other suitable container so that the sediment 21 is approximately 20-26 mm deep. This depth is important because it is necessary to both cover the cut sufficiently and provide proper filtration, but yet allow transport of nutrient to the phloem by passage of the liquid (water) therethrough. The freshly cut (as per FIGS. 1A and 1B) bud 16 stems 10 are inserted into the sediment 21. Irrespective of the degree of freshness, so long as the stem is capable of any uptake, the magnesium carbonate is drawn in by the phloem, the vascular system, and is consumed by the flower. Magnesium carbonate, of very fine mesh as described herein, is assimilated by the flower and provides the only (excellent) nutrient that the flower needs during its life as a cut flower. The nutritional value of this magnesium carbonate clearly obviates the use or need for sugar or other preservatives, even when the rose is displayed in a container as described herein. The magnesium carbonate has the added (filtration) advantage of preventing bacteria from reaching the base of the stem, while acting as an oxygen buffer by preventing water from having a direct contact (or oxidizing and drowning contacts) with the flower at the point of nutrient infusion. This retards considerably (almost to the point of elimination) the phenomenon of oxidation and its deleterious effects on freshly cut flowers.

Blanketing (Aromatic Essence) Technique

Full use of the invention's shelf life prolongation methodology is realized beginning with the cutting of the incipient bud and application of both "blanketing" and "carbonate/feeding" procedures of the invention. During research, it was recognized that flowers of the type being discussed had often been stored in the presence of more aromatic flowers and, although subjected to normal refrigeration techniques, appeared to have a retarded bloom development depending on the degree of confinement and the plentitude of aromatic flowers. After conducting a number of experiments, typified by the following, I realized that the essence of an aromatic flower has the capability of affecting (by retardation of oxidation) the speed at which a bud proceeds to a bloom.

Experimental

A bouquet of 18 roses, freshly cut in the bud stage, was placed in cold storage (about 40° F.) and wrapped singly thereabout in a porous wrapping paper. A tincture of essential oils, in this case oil of lavender, was infused into the paper or placed directly on the inner wrapping surface. Consistent results from use of this technique were exemplified by an extended dormant shelf life, in a state of bud, with extension of the nominal life of five days to an incredible 28 days, possibly more. Thereafter (the 28 days), the buds began to open and proceed to the full bloom stage.

With but the further definition of a few minor criteria, I submit that another remarkable and very valuable technique is now presented for extending the dormant shelf life of roses that are freshly cut and maintained under refrigeration of about 40° F. The value of the invention is seen in the fact, well known to florists, that roses have their highest commercial value in the bud state. Thus, preservation during this phase of flower development is most critical. Confinement with aromatic flowers or the essential oils of an aromatic flower, so as to provide a vapor blanket of the essence, must be maintained and care must be taken to maintain the refrigeration temperature within the given regime. A severe refrigeration, for example around 35° F., is known to discolor the pigmentation of roses and, especially red roses that turn bluish after subjection for several days at such low temperatures. It is also known that if the temperature is higher than 45° F., the process of blooming will begin and the value as a bud rose will diminish rapidly within ensuing days.

I have not digressed to matters such as packagings that would allow use of both techniques by the grower/harvester but suggest that a relatively simple and less costly technique would employ shipping crates embodying internal arrays of FIG. 2B tubelettes, each holding but one stem.

Those having ordinary skill in the art will recognize immediately the value of the instant invention with blanketing and carbonate/feeding techniques and will, through use of the invention consistent with the hereinafter appended claims, find it to be of inestimable value in acquiring greater customer satisfaction and promoting the industry as a whole.

What is claimed is:

1. A method for extending shipping storage shelf life of freshly cut flowers during subsequent transport and storage comprising confining the cut flowers in a closed atmosphere or aromatic flower essence and vapors while refrigerating the cut flowers at a temperature of no lower than 35° F. nor higher than 45° F.

2. The method of claim 1 wherein the essence derives from the non-contacting proximity of aromatic flowers such as lavender and rose or oils thereof which give off vapors to provide said atmosphere.

3. A method for extending display shelf life of a cut flower in which the flower stem is immersed in a moist environment at a temperature above 35° F., the method comprising:

prewashing expanded magnesium carbonate to obtain light magnesium carbonate;

providing, in a container which contains essentially clean water, a sedimentary layer of said light magnesium carbonate having a grain size sufficient to allow bacterial filtration, nutritional passage of dissolved said carbonate to the flower and oxygen buffering;

inserting the cut end of the flower into the sedimentary layer ensuring its complete envelopment by the layer so that the end thereof receives water filtered only through the layer; and subjecting the flower, to the extent possible, to an aromatic essence of any aromatic flower or oil and vapors thereof.

4. The method of claim 3 wherein the sedimentary layer is about 20–26 mm thick.

5. The method of claim 3 wherein the grain size is about 2–20 microns.

6. A method for performing a commercially expedient freshness test on a cut flower, said test comprising:

preparing a suspension of silica particulate;

dipping a freshly cut end of a flower undergoing said test into the suspension for a first predetermined time; and removing the flower undergoing said test and observing the freshly cut end only after a second predetermined time for specific indicia of freshness.

7. The method of claim 6 wherein preparing comprises making an aqueous suspension of silica having about 325 mesh granularity.

8. The method of claim 7 wherein a first predetermined time of dipping is about 20 seconds.

9. The method of claim 8 wherein a second predetermined time of observing is about 30 seconds.

10. The method of claim 6 wherein specific indicia of freshness comprise granular silica deposits.

* * * * *